(12) United States Patent
Schnitzer et al.

(10) Patent No.: US 9,519,961 B2
(45) Date of Patent: Dec. 13, 2016

(54) METHODS AND SYSTEMS OF IMAGING CUT STONES

(71) Applicant: Sarine Color Technologies Ltd., Kfar Saba (IL)

(72) Inventors: Shai Schnitzer, Tel-Aviv (IL); Yaniv Ben-Hagai, Moshav Elishama (IL)

(73) Assignee: Sarine Color Technologies Ltd., Kfar Saba (IL)

( * ) Notice: Subject to any disclaimer, the term of this patent is extended or adjusted under 35 U.S.C. 154(b) by 0 days.

(21) Appl. No.: 14/874,889

(22) Filed: Oct. 5, 2015

(65) Prior Publication Data

US 2016/0027166 A1    Jan. 28, 2016

Related U.S. Application Data

(63) Continuation of application No. 13/255,920, filed as application No. PCT/IL2010/000211 on Mar. 11, 2010, now Pat. No. 9,151,717.

(60) Provisional application No. 61/202,537, filed on Mar. 11, 2009.

(51) Int. Cl.

| G06T 7/00 | (2006.01) |
| G01N 21/87 | (2006.01) |
| G01N 33/38 | (2006.01) |
| G06K 9/52 | (2006.01) |
| G06T 7/60 | (2006.01) |
| G06T 15/08 | (2011.01) |
| H04N 5/225 | (2006.01) |
| H04N 5/232 | (2006.01) |
| H04N 5/262 | (2006.01) |

(52) U.S. Cl.
CPC ............ *G06T 7/0004* (2013.01); *G01N 21/87* (2013.01); *G01N 33/381* (2013.01); *G06K 9/52* (2013.01); *G06T 7/0042* (2013.01); *G06T 7/60* (2013.01); *G06T 15/08* (2013.01); *H04N 5/2256* (2013.01); *H04N 5/23216* (2013.01); *H04N 5/23245* (2013.01); *H04N 5/2628* (2013.01); *G06T 2207/30108* (2013.01)

(58) Field of Classification Search
CPC ........ G01N 21/87; G01N 33/381; G06K 9/52; H04N 5/23245; H04N 5/23216; H04N 5/2628; H04N 5/2256; G06T 2207/30108; G06T 15/08; G06T 7/60; G06T 7/0042; G06T 7/0004
USPC ......................................... 348/94
See application file for complete search history.

(56) References Cited

U.S. PATENT DOCUMENTS

| 4,417,564 | A | * | 11/1983 | Lawrence | ............... | B24B 9/162 |
| | | | | | | 125/30.01 |
| 5,615,005 | A | * | 3/1997 | Valente | .................. | G01J 3/0251 |
| | | | | | | 356/30 |
| 6,567,156 | B1 | * | 5/2003 | Kerner | .................... | G01N 21/87 |
| | | | | | | 356/30 |

(Continued)

*Primary Examiner* — Christopher S Kelley
*Assistant Examiner* — Zhihan Zhou
(74) *Attorney, Agent, or Firm* — Greenberg Traurig, LLP

(57) ABSTRACT

A method of imaging a cut stone. The method comprises a) identifying an orientation of a cut stone (202), b) creating a volumetric model of the cut stone according to the orientation (203), c) capturing a plurality of images of the cut stone from a plurality of viewing angles around the cut stone (204), d) cropping a plurality of segments depicting the cut stone from the plurality of images using the volumetric model (205), and e) generating a volumetric image of the cut stone from the plurality of segments (207,208).

11 Claims, 13 Drawing Sheets

(56) References Cited

U.S. PATENT DOCUMENTS

| | | | |
|---|---|---|---|
| 7,420,657 B2 * | 9/2008 | Sasian | G01N 21/8806 356/30 |
| 2002/0048396 A1 * | 4/2002 | Bewley, Jr. | B44B 1/006 382/154 |
| 2003/0223054 A1 * | 12/2003 | Warwick | G06K 19/06037 356/30 |
| 2005/0187831 A1 * | 8/2005 | Gershburg | G06Q 30/0643 705/27.2 |
| 2006/0066877 A1 * | 3/2006 | Benzano | G01N 21/87 356/603 |
| 2007/0157667 A1 * | 7/2007 | Maltezos | A44C 17/00 63/32 |
| 2008/0231833 A1 * | 9/2008 | Shlezinger | G01N 21/15 356/30 |
| 2010/0111354 A1 * | 5/2010 | Hornabrook | G01N 21/87 382/100 |

* cited by examiner

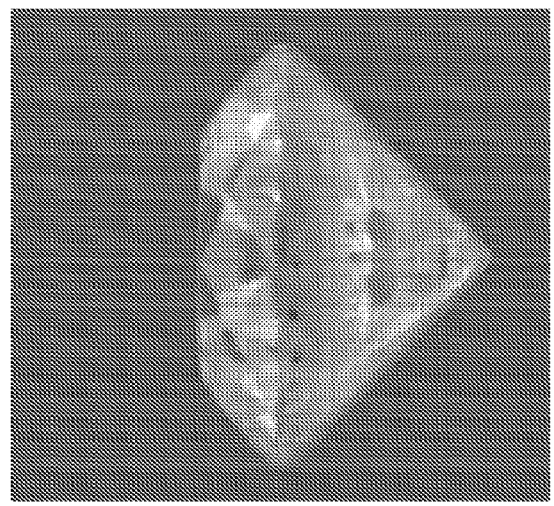
FIG. 16
FIG. 15
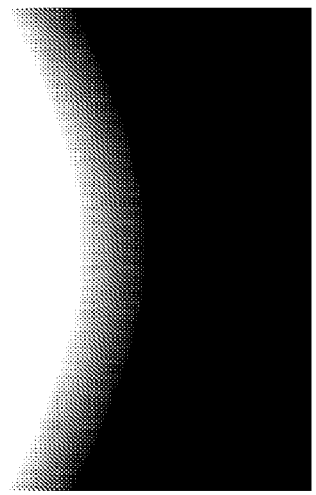
FIG. 14

METHODS AND SYSTEMS OF IMAGING CUT STONES

RELATED APPLICATION

This application is a continuation of U.S. patent application Ser. No. 13/255,920, filed on Sep. 12, 2011, which is a National Phase of International Application No. PCT/US2010/000211, filed on Mar. 11, 2010, which claims priority of U.S. Provisional Patent Application No. 61/202,537, filed on Mar. 11, 2009, the entirety of which are hereby incorporated by reference.

FIELD AND BACKGROUND OF THE INVENTION

The present invention, in some embodiments thereof, relates to imaging and, more particularly, but not exclusively, to methods and systems of imaging cut stones.

Cut stones, such as diamonds, are often analyzed based upon their visual appearance to the human eye. As such, a cut stone's visual appearance is a primary indicator of the quality of the diamond. Accordingly, because diamond quality is substantially based on human visual perception, diamond analysis requires the exercise of judgment, the formation of opinions and the ability to draw fine distinctions based on visual comparisons.

With regard to diamond analysis, the foundation of diamond analysis comprises analysis of the Four C's (color, clarity, cut and carat weight), a method of analysis defined by the Gemological Institute of America (GIA). Two of the Four C's, color and clarity, are evaluated along a scale or continuum. In the case of colorless to light-yellow colored diamonds, an analysis is made along what is commonly referred to as the GIA D to Z scale. The GIA D to Z color scale, ranging from colorless to yellow, is an international standard which has been calibrated to GIA's master diamonds since its development.

Usually, diamond quality analysis is performed by a team of trained individuals who visually inspect a diamond for features such as inclusions and structural flaws. This time-intensive process involves numerous inspections, measurements and checks by each individual. The process also involves quality control and may include a variety of non-destructive tests to identify treatments, fillings or other defects that may affect the quality of a specimen.

During the last years methods which involve cut stone imaging have been developed. For example, U.S. Pat. No. 7,461,017, filed on Apr. 30, 2004 describes system and method of providing informational certificates concerning characteristics of jewelry items to customers. The system includes a terminal having a user interface configured to receive user input information concerning at least a first characteristic of a first jewelry item, a camera device capable of obtaining image information regarding at least a part of the first jewelry item, and a printing device at least temporarily coupled to the terminal and the camera device and capable of printing a first certificate, where the first certificate includes a first portion of information based upon the user input information and a second portion of information based upon the image information, and where the terminal, the camera device and the printing device are proximate a local point of sale of the first jewelry item.

Other methods and systems have been developed to improve or facilitate the diamond evaluation process, for example U.S. Pat. No. 7,136,154 filed on Jun. 9, 2003 describes a gemstone rating system which is used for rating the cut of diamonds in which particular cuts and features are measured and the results compared with and provided with a predetermined score depending upon deviations from a theoretical perfect cut; and wherein the deviation scores are summed and then subtracted from an initially perfect score to provide a universally comparable indication of quality of cut.

SUMMARY OF THE INVENTION

According to some embodiments of the present invention, there is provided a method of imaging a cut stone. The method comprises a) identifying an orientation of a cut stone, b) creating a volumetric model of the cut stone according to the orientation, c) capturing a plurality of images of the cut stone from a plurality of viewing angles around the cut stone, d) cropping a plurality of segments depicting the cut stone from the plurality of images using the volumetric model, and e) generating a volumetric image of the cut stone from the plurality of segments.

Optionally, the method further comprises presenting the volumetric image to allow imaging the cut stone from any of the plurality of viewing angles.

Optionally, the plurality of segments depicting the cut stone in a first placement, further comprising reposition the cut stone in a second placement and repeating the b)-d) to create a plurality of additional segments depicting the cut stone in the second placement, the generating comprising merging between the plurality of segments and the plurality of additional segments to generate the volumetric image.

More optionally, the generating comprises correlating between the plurality of segments and the plurality of additional segments.

Optionally, the identifying comprises capturing a plurality of calibration images of the cut stone from a plurality of point of view around the cut stone and estimating the orientation according to an analysis of the plurality of calibration images.

Optionally, the creating comprises capturing a plurality of modeling images of the cut stone from a plurality of point of view around the cut stone and creating the volumetric model according to an analysis of the plurality of modeling images.

More optionally, the identifying comprises calculating a scanning path according to the orientation and maneuvering at least one image sensor to capture the plurality of modeling images according to the scanning path.

Optionally, the capturing is performed by maneuvering at least one image sensor to capture the plurality of images according to at least one of the volumetric model and the orientation.

Optionally, the capturing comprises capturing the plurality of images from a plurality of viewing angles on a surface of a virtual sphere around the cut stone.

Optionally, the method further comprises illuminating the cut stone with light diffused from a plurality of reflecting elements.

According to some embodiments of the present invention, there is provided a system of imaging a cut stone. The system comprises a holder for mounting a cut stone, at least one image sensor, an image sensor actuator which maneuvers the at least one image sensor to capture a plurality of images of the cut stone from a plurality of viewing angles around the cut stone, an image capturing module which analyses the plurality of images to compute a volumetric model of the cut stone and crops a plurality of segments depicting the cut stone from a group of the plurality of images according to the volumetric model, a reconstruction module which reconstructs a volumetric image of the cut stone from the plurality of segments, and an output unit which outputs the volumetric image to allow imaging the cut stone from any of the plurality of viewing angles.

Optionally, the image capturing module which analyses the plurality of images to compute an orientation of the cut stone to compute a scanning pattern, further comprising a controller which instructs the holder and the image sensor actuator to respectively rotate the cut stone and the image sensor according to the scanning pattern when computing the volumetric model.

More optionally, the system further comprises a controller which instructs the holder and the image sensor actuator to respectively rotate the cut stone and the image sensor to capture the group from the plurality of viewing angles.

Optionally, the viewing angles are on a surface of a virtual sphere around the cut stone.

Optionally, the holder is set for rotating the cut stone around a first rotation axis, the image sensor actuator being configured for rotating the image sensor around a second rotation axis, the first and second rotation axes are perpendicular to one another, the rotating being performed to maneuver the at least image sensor among the plurality of viewing angles.

Optionally, the system comprises a background element set to maneuver so that each image depicts the cut stone with the background element at the back.

Optionally, the system comprises a lighting setup which illuminates the cut stone and a light diffuser which is sized and shaped for being placed between the cut stone and the at least one image sensor, the light diffuser having at least one slit for allowing the at least one image sensor to capture the plurality of images from the plurality of viewing angles.

Optionally, the system comprises at least one illumination source placed in the light diffuser to increase the exposure of the at least one image sensor.

Optionally, the system comprises a vacuum pressure generator for maintaining the cut stone on the holder.

Optionally, the system comprises an illumination source set to be maneuvered with the at least image sensor so as to illuminate the cut stone from the plurality of viewing angles.

According to some embodiments of the present invention, there is provided a method of imaging a cut stone. The method comprises a) generating a first partial volumetric image of a first part of a cut stone from a plurality of images taken from a plurality of viewing angles around the first part, b) generating a second partial volumetric image of a second part of the cut stone from a plurality of additional images taken from a plurality of additional viewing angles around the second part, c) merging the first and second partial volumetric images to generate a volumetric image of the cut stone, and d) outputting the volumetric image.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 14 is a includes a merged and correlated segment taken from a volumetric image of the cut stone;

FIG. 15 depicts an exemplary merge mask gradient, according to some embodiments of the present invention; and FIG. 16 depicts an exemplary image taken from an exemplary merged volumetric image, according to some embodiments of the present invention.

DESCRIPTION OF EMBODIMENTS OF THE INVENTION

Figure 1:
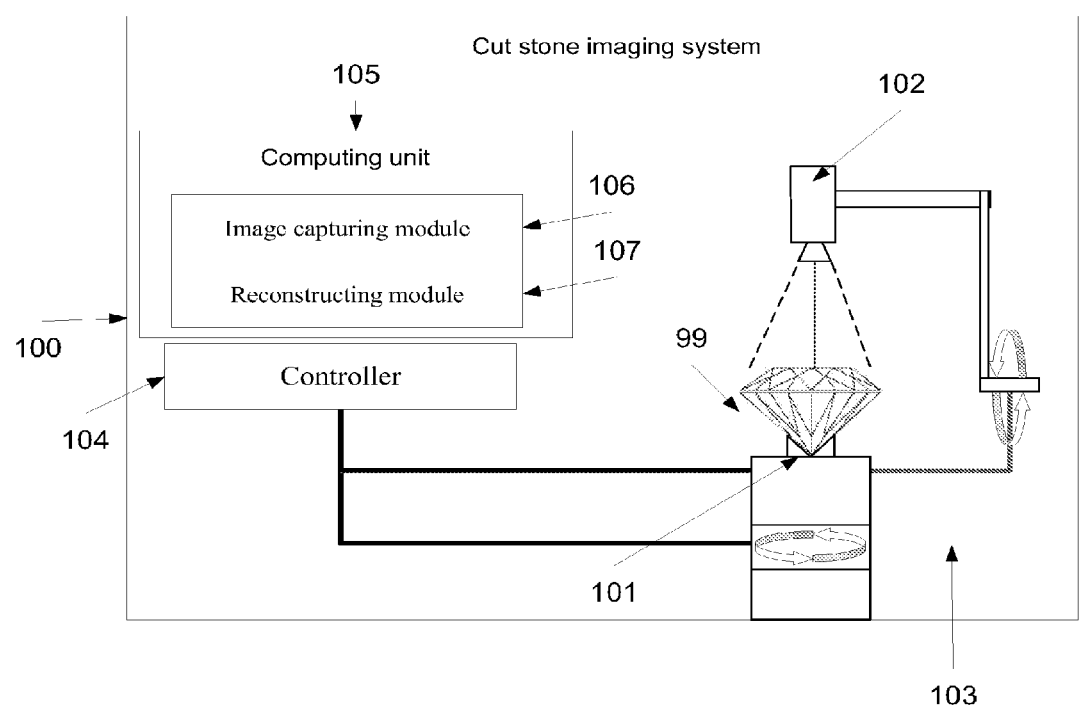
FIG. 1 is a schematic illustration of a cut stone imaging system for generating a volumetric image of a cut stone, according to some embodiments of the present invention.

The present invention, in some embodiments thereof, relates to imaging and, more particularly, but not exclusively, to methods and systems of imaging cut stones.

According to some embodiments of the present invention, there is provided a method and a system of automatically or semi automatically generating a volumetric image of a cut stone, such as a diamond, that allows a viewer to view the imaged cut stone from a plurality of different viewing angles. For example, the volumetric image images the cut stone from between about 60 and about 360 possible viewing angles, for example 144, in between about 5 and 180 different planes passing through the cut stone and having about 1° separating between them.

The system includes a holder, optionally rotating, for mounting a cut stone and one or more image sensors which are mounted on one or more image sensor actuators. The image sensor actuator maneuvers the image sensor to capture a plurality of images of the cut stone from a plurality of viewing angles around the cut stone. Optionally, the image sensor and the holder have perpendicular rotation axes. The system further includes an image capturing module which analyses the plurality of images to compute a volumetric model of the cut stone and crops a plurality of segments depicting the cut stone from a group of the images according to the volumetric model. The system further includes a reconstruction module which reconstructs a volumetric image of the cut stone from the plurality of segments and an output unit which outputs the volumetric image to allow imaging the cut stone from any of a plurality of viewing angles.

According to some embodiments of the present invention there is provided a method of imaging a cut stone. The method includes identifying an orientation of a cut stone, for example by analyzing a set of calibration images taken from a plurality of circumferential points around the cut stone. Then, a volumetric model of the cut stone is created using the orientation, for example by acquiring and analyzing a plurality of modeling images captured along a scan path calculated according to the orientation. Now, images of the cut stone are captured from a plurality of viewing angles around the cut stone, for example from a plurality of viewing angles on a virtual sphere surrounding the cut stone. Now, segments depicting the cut stone are cropped from the images using the volumetric model. This process allows generating a volumetric image of the cut stone from the plurality of segments.

According to some embodiments of the present invention there is provided a method of imaging a cut stone using partial volumetric images. The method is based on a first partial volumetric image of a first part of a cut stone generated from a plurality of images taken from a plurality of viewing angles around the first part and a second partial volumetric image of a second part of the cut stone generated from a plurality of additional images taken from a plurality of additional viewing angles around the second part. These images are optionally taken using the system outlined above and described below. This allows merging the first and second partial volumetric images to generate a volumetric image of the cut stone and outputting the volumetric image, for example for display.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of a cut stone imaging system 100 of generating a volumetric image of a cut stone, according to some embodiments of the present invention. As used herein, a volumetric image means a dataset that provides a multi dimensional representation of the cut stone, for example a three dimensional representation. The volumetric image may be a set of a plurality of images, each depicting the cut stone from a different viewing angle and/or a 3D element which is generated based on the plurality of images.

As used herein, a cut stone 99 means a cut and optionally polished piece of mineral, such as a diamond, gemstone and the like. The cut may be, for example round brilliant cut, mixed cut, rose cut, and/or step cut. The cuts may be as defined in the following standards: accredited gem appraisers (AGA), American Standard, practical fine cut, Scandinavian standard, Eulitz brilliant, ideal brilliant, and parker brilliant. This standard is incorporated herein by reference.

Figure 2:
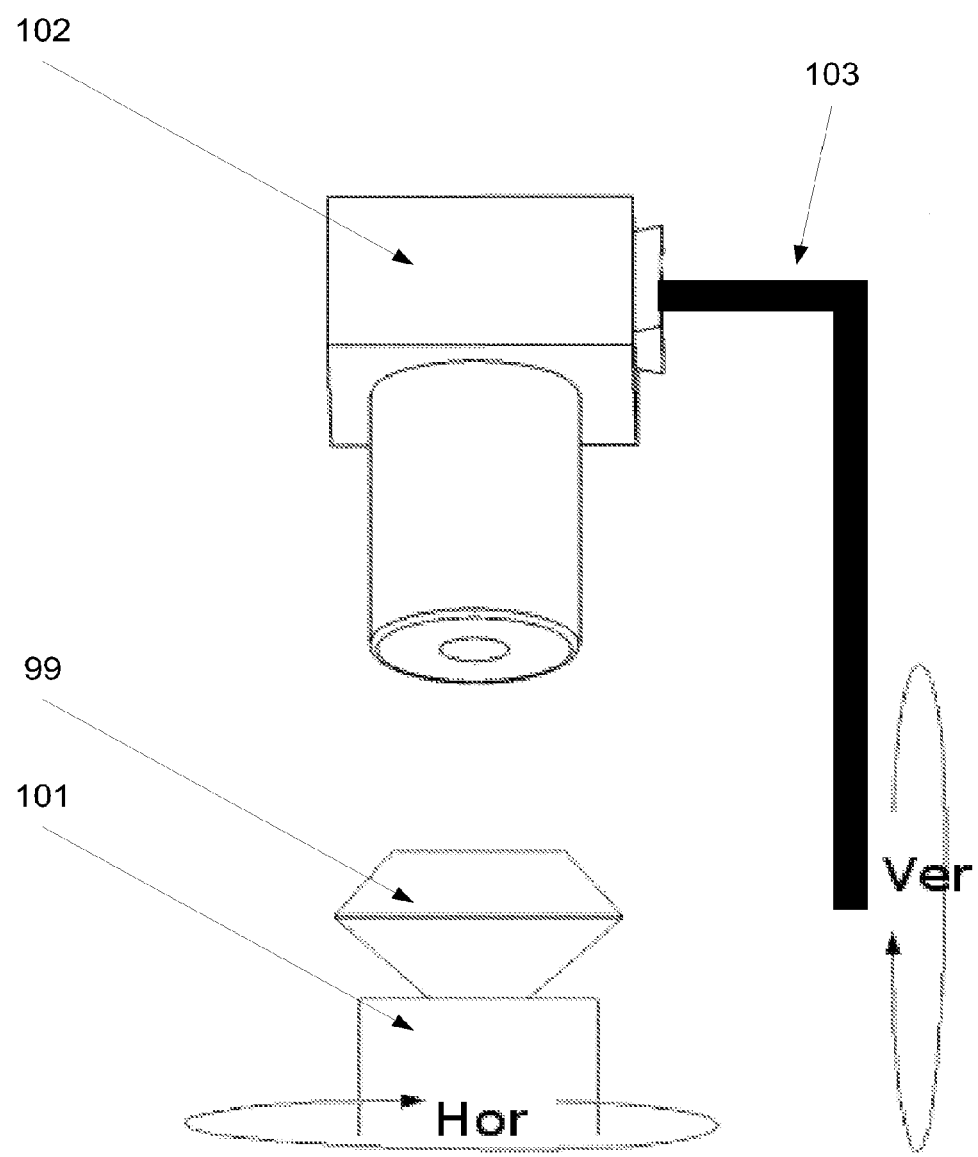
FIG. 2 is a schematic illustration of an image sensor actuator set to maneuver an image sensor around a cut stone in a plane which is parallel to a rotation axis of a holder on which the cut stone is mounted, according to some embodiments of the present invention.

The cut stone imaging system 100 includes a holder 101, optionally rotating, for mounting a cut stone 99 and one or more image sensors 102, such as camera, for brevity referred to herein as an image sensor 102, which captures images of the cut stone 99. The image sensor 102 is connected to an image sensor actuator 103 which maneuvers it to capture images of the cut stone 99 from a plurality of point of view around the holder. Optionally, the image sensor actuator 103 is a lever actuated by a motor, such as a step motor. Optionally, the image sensor actuator 103 supports the image sensor 102 so that its lens is at a distance of about 10 centimeters from the cut stone during the rotation. Optionally, as shown at FIG. 2 the image sensor actuator 103 is set to maneuver the image sensor 102 around the cut stone 99 in a plane parallel to the rotation axis of the holder 101. In such an embodiment, the rotation axis about which the image sensor 102 rotates is perpendicular to the rotation axis about which the cut stone 99 rotates. This rotation axis maintains the image sensor approximately in front of the center of the stone. These rotation axes allow imaging the cut stone 99 from any point on the surface of a virtual sphere around the cut stone 99. In order to image segments which are concealed by the holder, the cut stone 99 is imaged in two opposing placements, for example as described below and depicted in FIGS. 6A and 6B. The image sensor may be a charge coupled device (CCD) based sensor, a complementary metal oxide semiconductor (CMOS) based sensor and/ or any other sensor for capturing an image of a cut stone. Optionally, the image sensor 102 is 3 mega pixel MP sensor or more. Optionally, the image sensor 102 has a replaceable lens. In such a manner, various lenses, for example macro lens 16 mm, 25 mm, 30 mm, and/or 50 mm may be selected and used based on the size of the cut stone 99. Optionally, the image sensor 102 has a controllable focus, optionally determined according to the distance of the image sensor 102 from gemstone. The distance may be manually set, extracted from the volumetric model generated below, and/or estimated using a distance detector, such as a laser based distance detector. Optionally, various focus depths are used for the same area, for example for imaging the table. The focus may be changed by a focus motor inside the lens of the image sensor 102, changing the location of the image sensor, and/or lifting the gemstone during the scan, for example using an elevating element in the holder 101. Optionally, the image sensor 102 includes a microscope image sensor which allows capturing images for minor inclusions detection.

Figure 3:
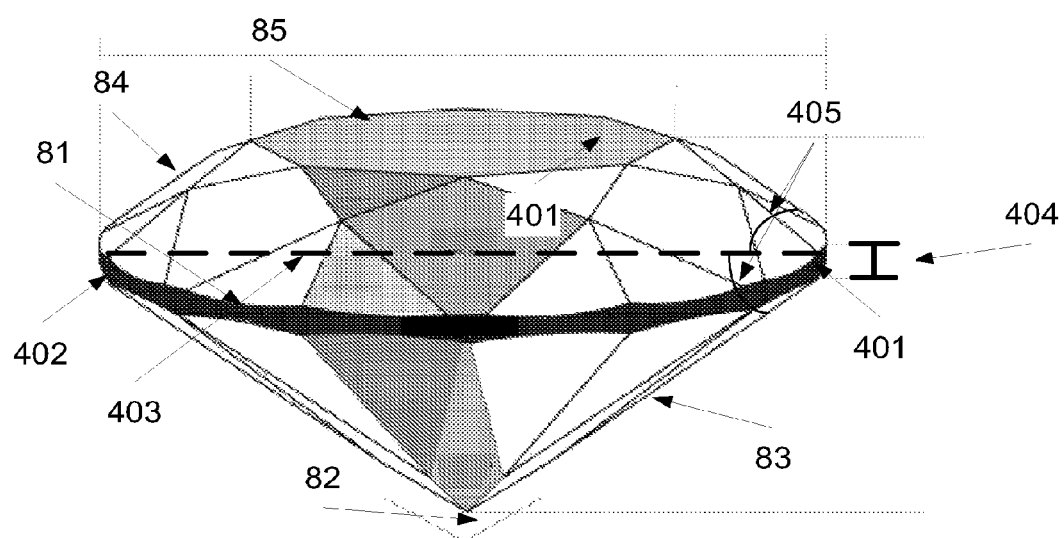
FIG. 3 is an exemplary schematic illustration of an exemplary cut stone for depicting terms used herein.

FIG. 3 is an exemplary schematic illustration of an exemplary cut stone 99 for depicting terms used herein. The girdle 81, the pavilion 83, the crown 84, the upper table 85 and the culet 82 are depicted with respective numerals. Optionally, the image sensor 101 includes an illumination source which is directed toward the area it images. Optionally, the image sensor 102 is placed behind a half transferable mirror and/or a white reflector to reduce reflection. Optionally, the lens of the image sensor 102 is provided with a white reflector.

The cut stone imaging system 100 further includes a computing unit 105, such as a personal computer, a laptop, a microprocessor and/or a digital signal processing (DSP) and controller 104 which controls the image sensor actuator 103. The computing unit 105 optionally hosts an image capturing module 106 which calculates motion scanning patterns for maneuvering the image sensor 102 and/or rotating the holder 101 and a reconstruction module 107 which reconstructs a volumetric image of the cut stone 99 by merging a plurality of cut stone images taken from a plurality of points of view by the image sensor 102 the cut stone 99 and/or the image sensor 102 are maneuvered. As the volumetric image is based on a plurality of images taken from a plurality of points of view around cut stone, it may allow a viewer to receive an image of the cut stone from every possible angle. As further described below, the volumetric image may not include pixels with estimated values and therefore provides genuine and reliable representation of the cut stone 99. The volumetric image which is generated below may be based only on images of the cut stone 99 and therefore does not require using external data sources, such as predefined models, estimated contours and the like. As such, the volumetric image may be used to accurately evaluate the cut stone.

Optionally, the system 100 includes a lighting setup of illuminating the cut stone 99 while it is imaged. This allows capturing images with clear view of the inclusions of the cut stone 99, while increasing the brightness of the cut stone 99. Optionally, compact florescent lamps and/or LEDs are used to provide neutral and homogeneous light.

The homogeneousness of the light allows merging images taken from different point of view on a virtual sphere encircling the cut stone 99 so as to form a volumetric image without or substantially without brightness differences. For example, the lighting set allows similarly illuminating both the pavilion conoid below the girdle 81 and the truncated crown conoid above the girdle 81 while they are imaged. For example, reference is now made to FIG. 4, which is a schematic illustration of a set of lamps 131 which are used to illuminate the cut stone 99 on the holder 101, according to some embodiments of the present invention. For example, the set of lamps 131 includes 6 LP 28 W cool white light bulbs which are positioned in the box.

Optionally, a background element is placed on the holder 101, to provide a background to the images captured by the image sensor 102. In such a manner, a background element, optionally black, rotates with the holder assures that the cut stone 99 is between the image sensor 102 and background element during the imaging process.

Figure 4:
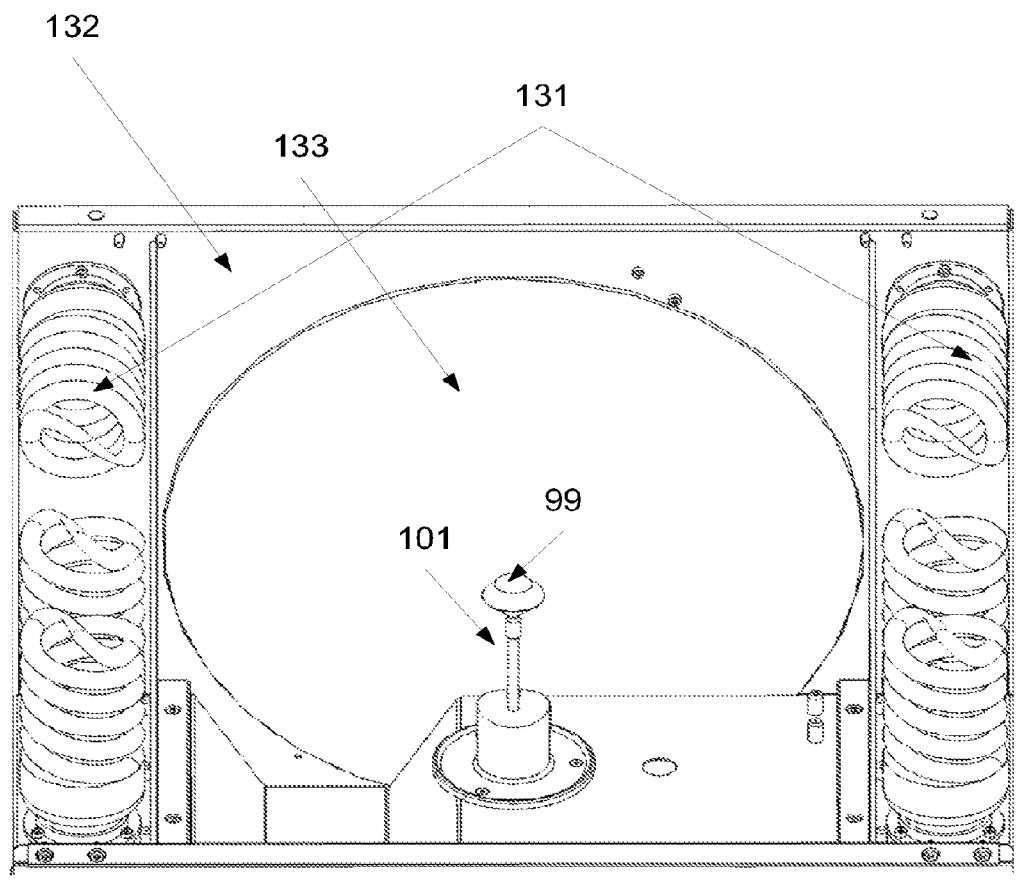
FIG. 4 is a schematic illustration of a light setup having a set of lamps which are used to illuminate the cut stone on the holder, according to some embodiments of the present invention.

As depicted in FIG. 4, the rotating holder 101 is placed at the center of a box, such as a 35×35×35 cm box, having inner walls covered with white surface. Optionally, the light setup includes a light diffuser, for example a 15 cm diameter white lusterless hemispherical or substantially hemispherical element. The hemispherical element is positioned so that its inner space is turned toward the holder 101 and the cut stone 99 and so that the cut stone 99 is positioned in front of the middle of the hemispherical element, for example 5 centimeter (cm) below the upper edge. Optionally, a vertical slot of about 2 cm wide is formed in the front side of the hemispherical element. Optionally, the distance between the cut stone 99 and the hemispherical element is about 110 mm. This vertical slot allows imaging the cut stone 99, for example by rotating the image sensor 102 so that its optical axis passes through the vertical slot. The vertical slot is optionally higher than the tip of the light bulbs so that no direct light gets into the hemisphere.

The light setup allows illuminating the cut stone 99 with light diffused from a plurality of reflecting elements, such as the walls of the box and/or the light diffuser. In such embodiments, light is optionally diffused a number of times, for example twice, in order to get homogeneous and soft illumination. For example a first diffusion is from the outer box 132 where the light is diffused evenly from the inner walls and the second diffusion is from the hemisphere where the light is focus towards the cut stone 99. The multiple diffusions induce a clear illumination of the internals parts of the cut stone 99. Such an illumination increases the sparkling of the facets of the cut stone 99 and cancels the effect of a direct reflection from surfaces of the cut stone 99, for example from the upper table 85. A clear view of the lower facets from inner space of a cut stone 99, such as a diamond, is also achieved.

Optionally, one or more illumination sources, such as an array of 3×3 big, white LEDs are positioned inside the hemisphere so as to illuminate that the cut stone 99 from a front position in relation to the slit. Optionally, each illumination source includes LEDs which are covered with a roughly polished acrylic glass foil in order to blur the sharp edges of the LEDs. In use, during the scanning process, the illumination source is energized to overexpose the image sensor 102 so that the image captures the outline of the cut stone, achieving harsh contrast between the stone and it's surrounding.

Figure 5:
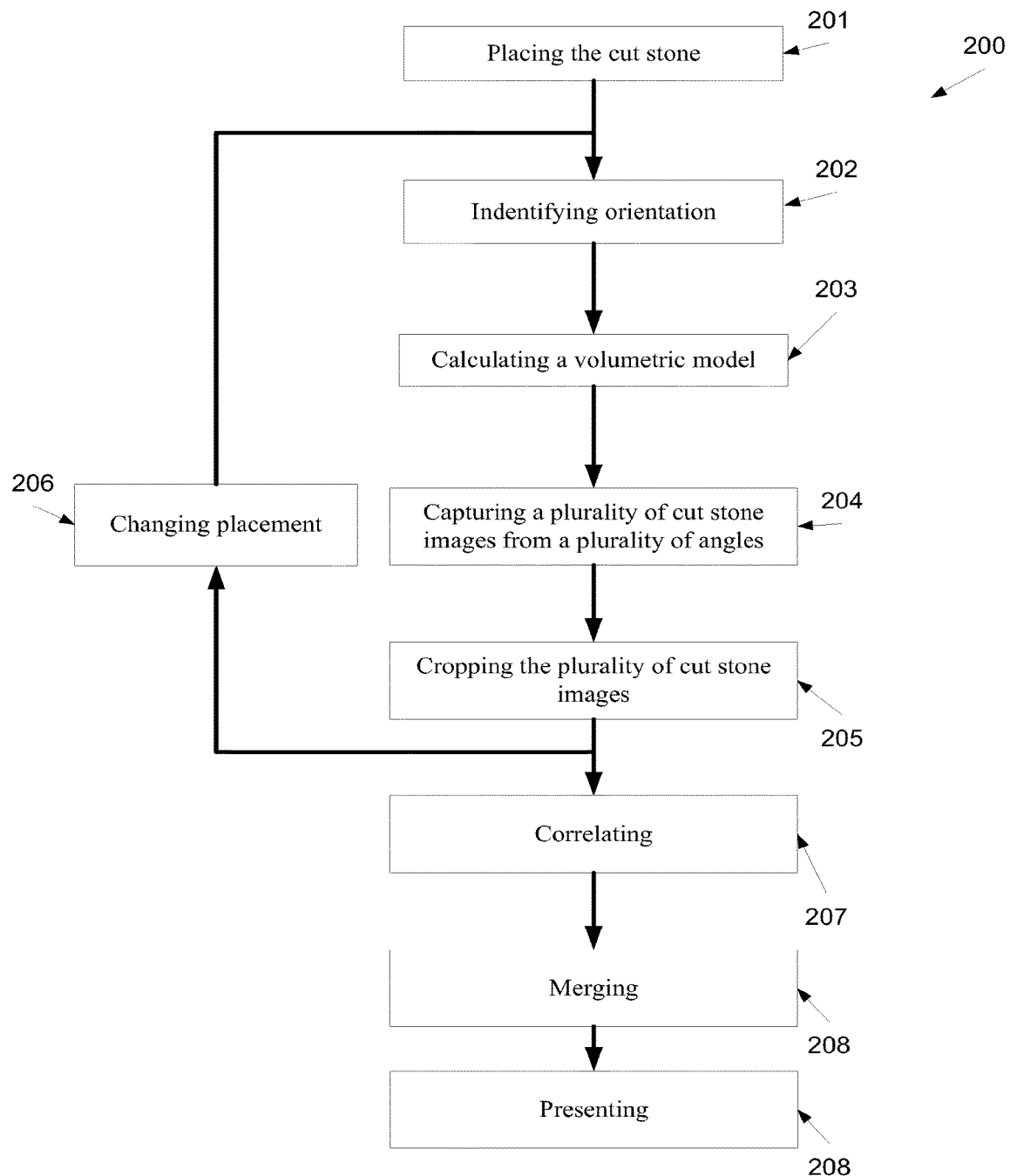
FIG. 5 is a flowchart of a method of imaging a cut stone, according to some embodiments of the present invention.

Reference is also made to FIG. 5, which is a flowchart of a method 200 of imaging a cut stone, according to some embodiments of the present invention.

Figure 6:
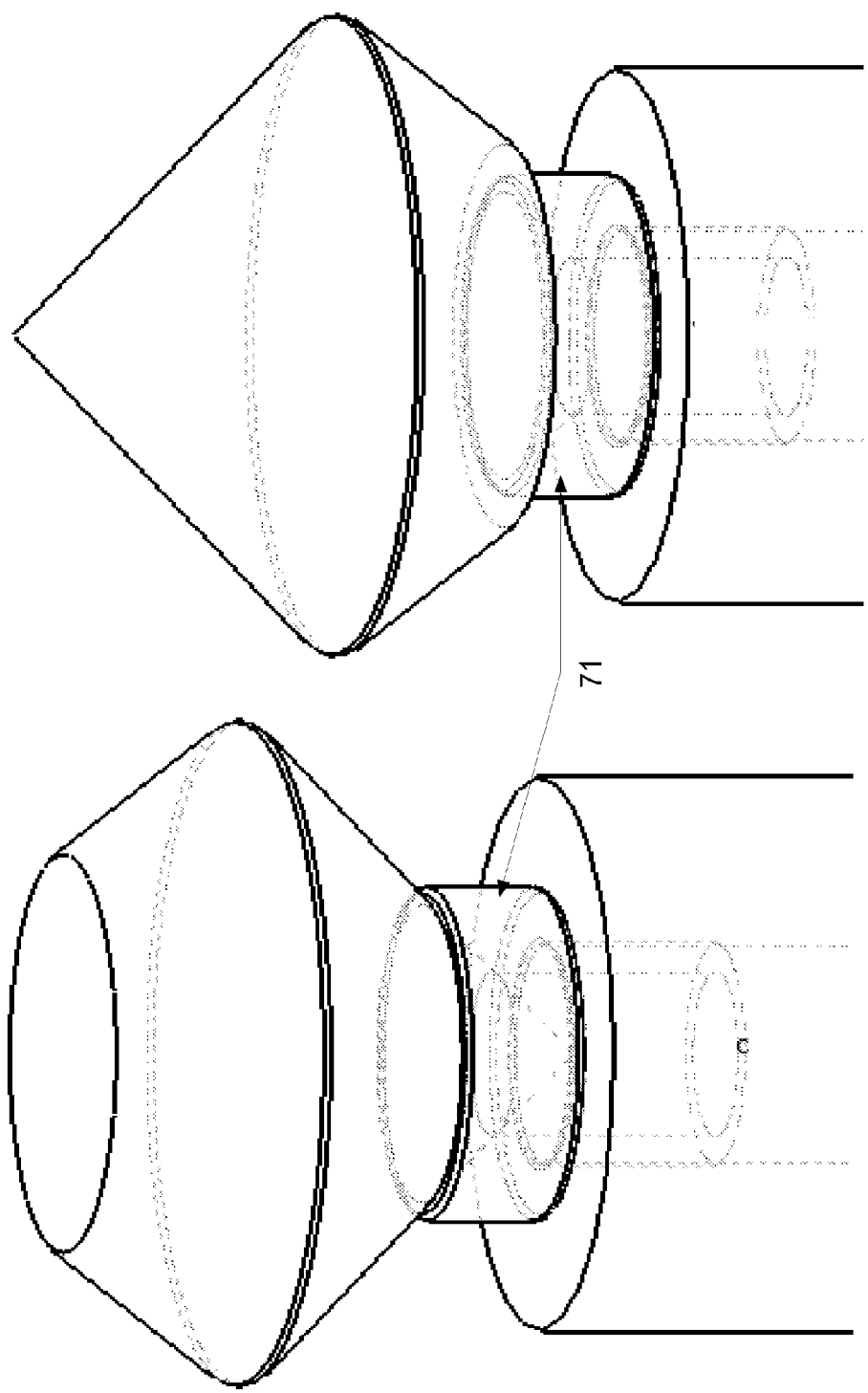
FIGS. 6A and 6B are schematic illustrations of an exemplary holder supporting exemplary cut stone in two different placements, according to some embodiments of the present invention.

First, as shown at 201 the cut stone 99 is mounted on the rotating holder 101, in a first placement, such as 101. For example, the cut stone 99 is placed as shown in FIG. 6A or as shown in FIG. 6B. These figures respectively depict first and second placements of the cut stone 99 in the holder 101. The first and second placements are opposing placements. For example, when the cut stone 99 is a brilliant cut diamond, the first placement is position the cut stone 99 with the table side up and the second placement is placing the cut stone 99 with the pavilion side up. The holder 101 optionally includes a supporting element 71, optionally annular, which holds the cut stone 99 so that the culet 82 is turned downward and the central axis of the cut stone 99 is perpendicular to the base of the holder 101. The holder allows mounting the cut stone 99 steady during the scanning process. Optionally, the supporting element 71 is detachable and replaceable. In such an embodiment, a supporting element, from a set of a plurality of supporting elements is selected according to the shape and/or size of the cut stone 99. In such a manner, specific stone cut may have adjusted support, for example round, oval, and the like.

Optionally, a vacuum pressure generator is used for maintaining the cut stone 99 on the holder 101, for example while it rotates. The vacuum pressure generator optionally includes a tube for generating vacuum attachment pressure on the cut stone 99. The tube is placed along the holder 101 so that is tip faces the supporting element 71. The tube is optionally a white straw made of glass or acrylic glass, coupled to a motor hollow shaft. The tune allows applying a vacuum pressure on the cut stone 99 during the scanning process. This pressure holds the cut stone 99 in place. Optionally, an adapter, optionally made of silicon, is attached to the tip of the tube so as to fit the surface of the cut stone 99. When the stone is up direction, the stone culet is covered by the adapter. When the stone is positioned down, the table of the stone is placed on the adapter.

Figure 7:
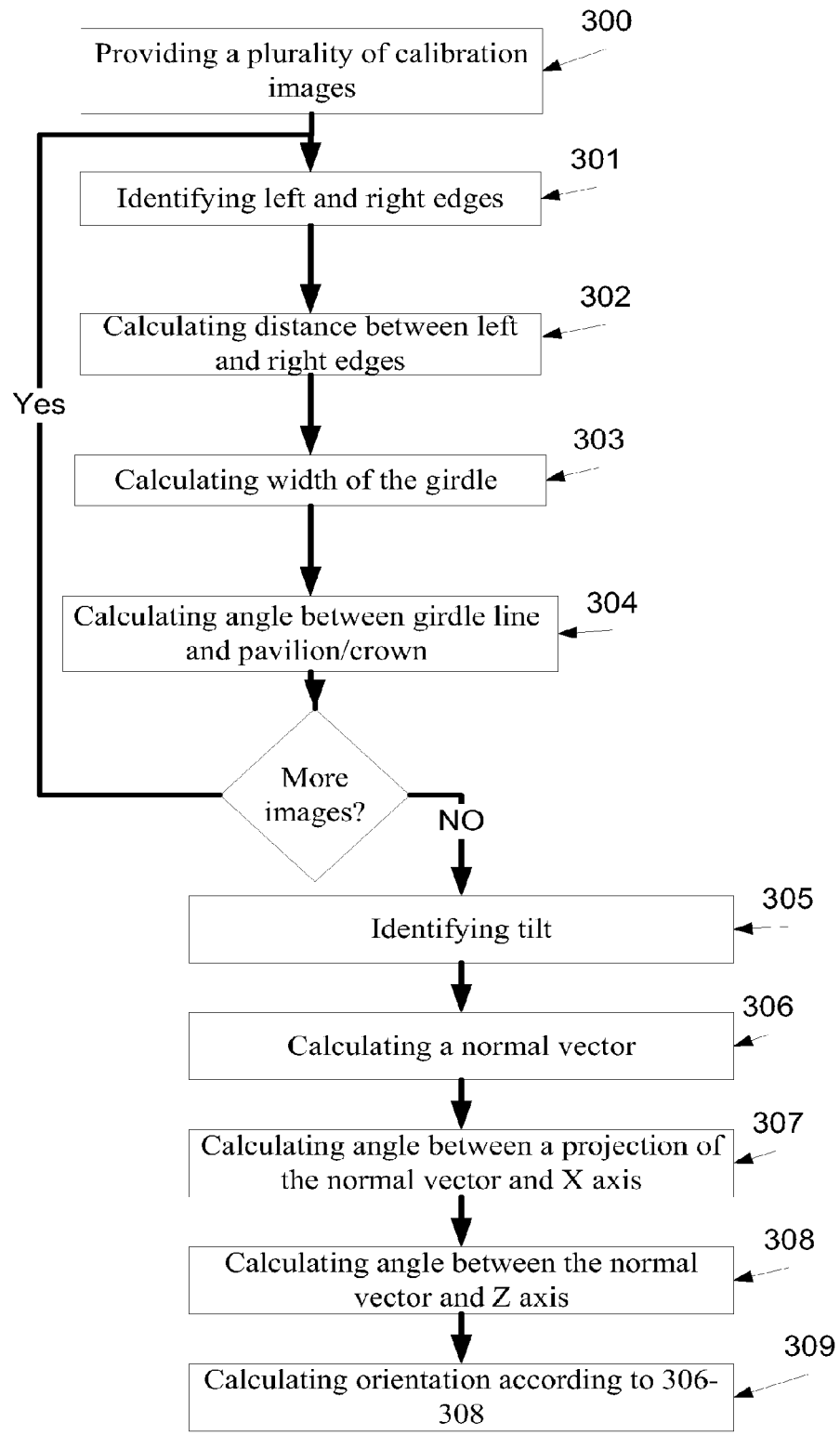
FIG. 7 is a flowchart of calculating the orientation of the cut stone in relation to a coordinate system, according to some embodiments of the present invention.

As shown at 202, the orientation of cut stone in its current placement is detected. Reference is now made to FIG. 7, which is a flowchart of calculating the orientation of the cut stone 99 in relation to a coordinate system, according to some embodiments of the present invention. For brevity, reference is also made to FIG. 3, which is an image of an exemplary cut stone, a diamond with a brilliant cut, as described above.

First, as shown at 300, a set of a plurality of calibration images depicting the cut stone 99 from a plurality of point of views around it are captured and provided. Optionally, these images, referred to herein as calibration images, are images taken when the optical axis of the circumferential image sensor 102 is substantially perpendicular to the girdle of the diamond 99. Optionally, the calibration images are taken around the diamond 99. For example, 360 images, each taken from a different angle between 0° and 259° degrees around the central axis of the cut stone 99, may be taken. Optionally, the horizontal angle difference between viewing angles of different images is between about 1° and about 6°, for example 2.5°. For clarity, a viewing angle means an angle of an axis originated from a point in and/or on the cut stone 99, optionally from the center of the cut stone 99. The angle may be in relation to the horizon and/or to a plane passing through the cut stone 99, optionally through the center of the cut stone 99. Now, the orientation of the cut stone 99 is calculated according to the calibration images.

Blocks 301-304 are repeated per calibration image. As shown at 301, the left and right edges 401, 402 of the girdle are found. Optionally, the calibration image is processed using a high pass filter. Then, two sub images are cropped around coordinates of previously identified left and right edges 401, 402 in a previously captured calibration image where the left and right edges in the first are identified by following the contour of the gemstone 99, optionally, from the highest point thereof in relation to the horizon. Each cropped image is filled using a convex hull algorithm. This allows marking the left or the right edges 401, 402 in it as the average of the 5 horizontal pixels which are the most distant from the center of the diamond, optionally identified according to the location of the culet 82.

As shown at 302, as shown at 403, the distance between the left and right edges 401 is calculated. This distance may be referred to herein as a girdle line length. As shown at 303, the width of the girdle 404 is calculated. This width may be referred to herein as a girdle width. As shown at 304, an angle 405 between a line that connects the left and right edges 401 and the pavilion 83 or the crown 84, depends on the positioning of the cut stone 99, is performed.

The data collected for each calibration image each 302-304 is stored in a plurality of vectors. The left and right edges in each image the distance between the left and right edges in each image is documented in an distance vector, the width of the girdle 402 in each image is documented in a girdle width vector, and the angle between a line that connects the left and right edges and the pavilion/crown in each image is documented in an inclination vector or an angle vector. Optionally, the coordinates are determined with respect to the coordinates of the circumferential image sensor 102 around the girdle 402. These vectors provide a mapping of perimeters of the cut stone 99 and allow calculating the orientation of the cut stone 99.

Figure 8:
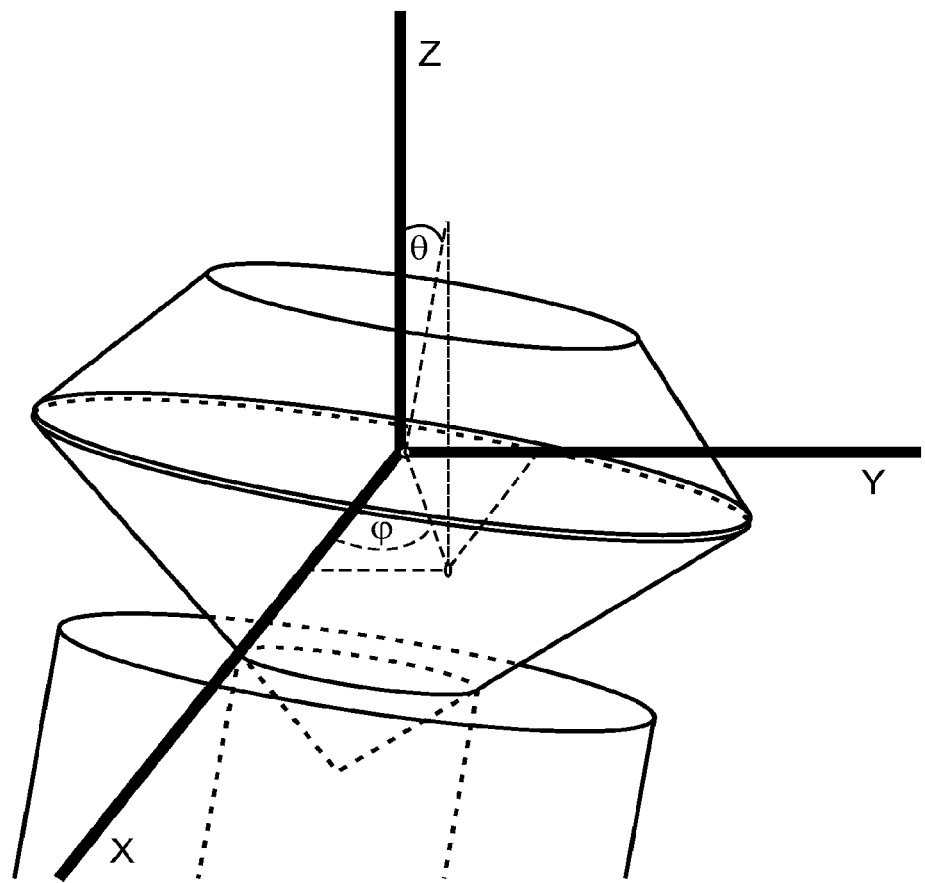
FIG. 8 is a schematic illustration of the cut stone on a holder in relation to the exemplary coordinate system, according to some embodiments of the present invention.

The cut stone 99 is oriented in relation to a coordinate system assigned in a three dimensional space. As shown at 305, the tilt of the cut stone 99 in relation to a horizontal plane of the coordinate system is estimated, for example by calculating the average angle between the average girdle line and the horizontal plane. Now, as shown at 306, the normal vector of the cut stone 99 is calculated according to the vectors. This allows, as shown at 307, calculating the angle between a projection of the normal vector on the horizontal plane and X axis of the coordinate system, referred to herein as phi ($\Phi$) and, as shown at 308, the angle between the normal vector and Z axis of the coordinate system, referred to herein as theta ($\Theta$). Optionally, the phi and the theta are calculated after the effect of the tilt is cancelled. For clarity, an exemplary coordinate system phi ($\Phi$) and theta ($\Theta$) are marked in FIG. 8 which is a schematic illustration of the cut stone 99 on a holder 101 in relation to the exemplary coordinate system, according to some embodiments of the present invention.

Now, as shown at 309, the tilt, theta and phi are used for calculating the orientation of the cut stone 99. In should be noted that theta is the amplitude of the sine created by the angle between the left and the right edges in all the images and phi is the rotation angle of the stone, in which the angle between the girdle and the horizontal axis is maximal (equal to the theta).

Reference is now made, one again, to FIG. 5. After the orientation of the cut stone 99 is calculated, a volumetric model of the cut stone in the current placement is evaluated as shown at 203.

Figure 9:
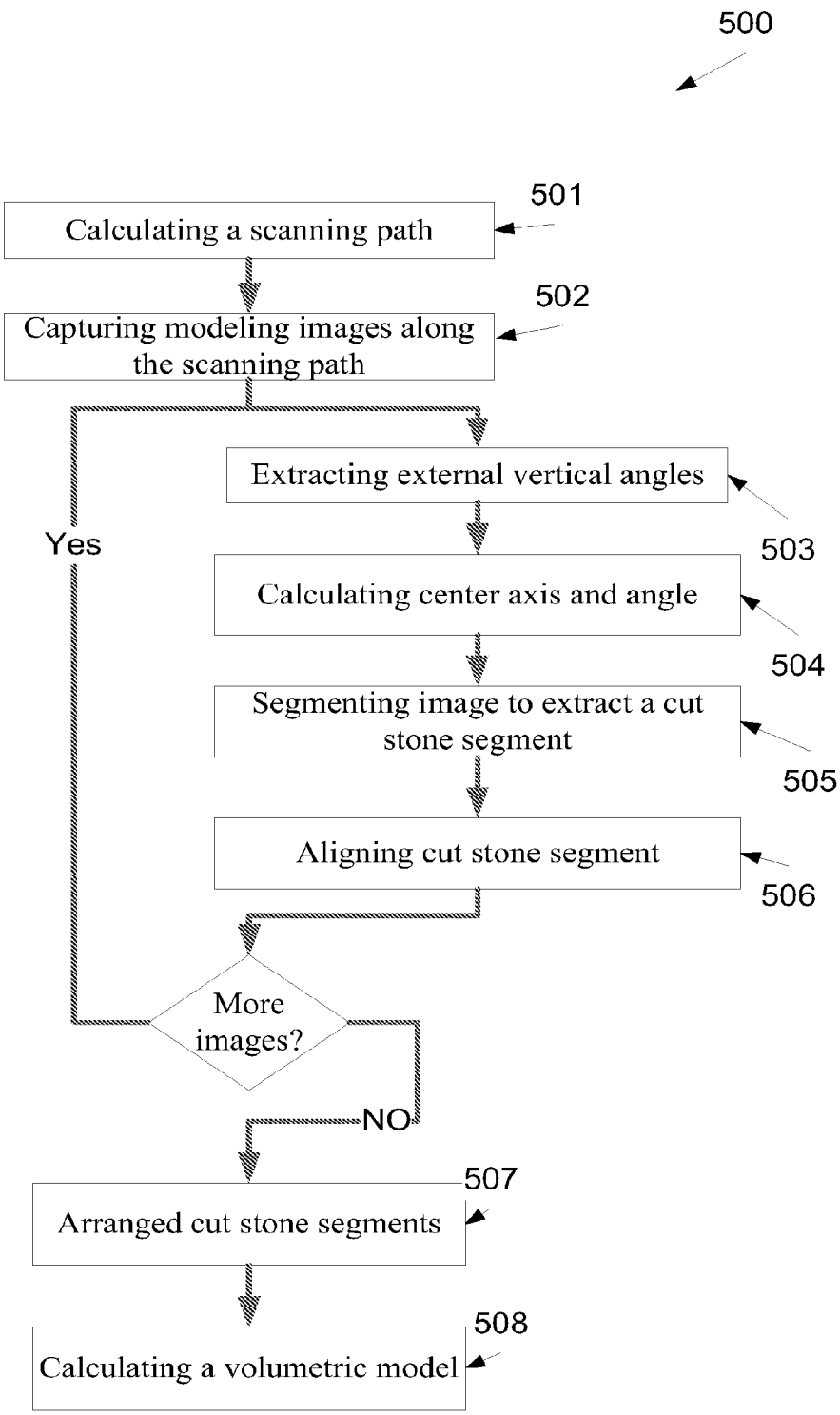
FIG. 9 is a flowchart of a method of generating a volumetric model based on a plurality of circumferential images, according to some embodiments of the present invention.

Reference is now made to FIG. 9, which is a flowchart of a method of generating a volumetric model based on a plurality of circumferential images, according to some embodiments of the present invention.

First, as shown at 501, a scanning path is calculated according to the orientation estimated in 202. Optionally, the motion scanning path is calculated by canceling the effect of the tilt and theta distortions which are calculated for each calibration image, as described above.

This allows, as shown at 502, maneuvering the image sensor 102 along the motion scanning path so that its optical axis is substantially perpendicular to the girdle of the cut stone 99. While the image sensor 102 is maneuvered along the motion scanning paths, a second set of images is captured, referred to herein as modeling images. Segments from these images are merged to reconstruct a volumetric model of the cut stone 99, as further described below. In use, the image sensor actuator 103 optionally changes the elevation and/or the angle of the image sensor 102 in relation to the horizon so that the image sensor 102 faces the girdle all along the motion scanning path. Optionally, the amplitude of the motion in each circumferential point of view is calculated according to the theta computed according to a calibration image taken from the same circumferential point of view. In such an embodiment, the cut stone 99 in the captured image is tilted in the captured image while the girdle is straight.

Figure 10:
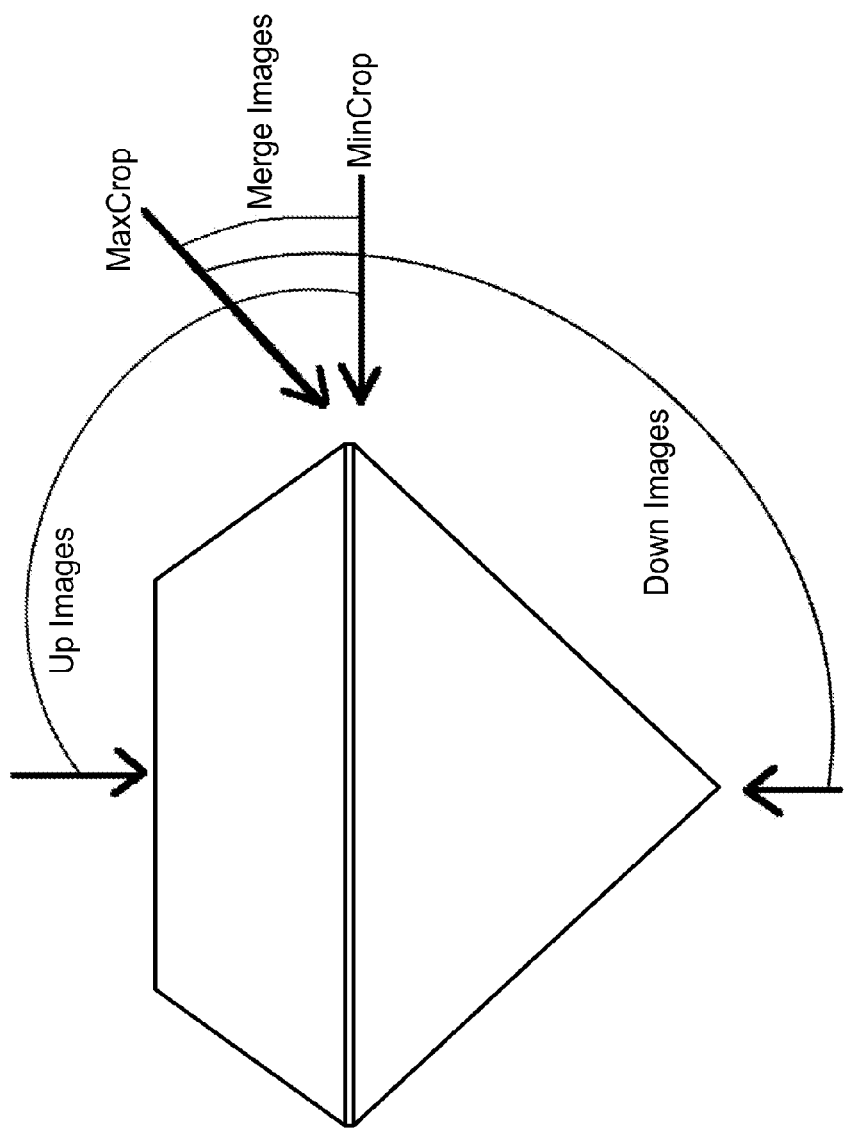
FIG. 10 is schematic illustration of external vertical angles of the cut stone, according to some embodiments of the present invention.

For each image the following is performed. First, as shown at 503, external vertical angles are extracted. For clarity, reference is now also made to FIG. 10, which is schematic illustration of external vertical angles of the cut stone 99. Optionally, the external vertical angles are angles defined according to the view vision of the image sensor 102 when the cut stone 99 is in the first and second placements. For example the external vertical angles include the vertical angle which below it the table portion of the cut stone 99 is not clearly visible when the table faces up is imaged, referred to herein as a MinCrop, the vertical angle which above it the culet is not clearly visible when the pavilion faces up and imaged, referred to herein as a MaxCrop. These angles allow merging between images which fully depict the pavilion side of the diamond and images which fully depict the table side of the diamond. The external vertical angles optionally include the external vertical angles of the left and right edges. It should be noted that though pavilion and table are for describing the placements and/or sides of the cut stone 99, cut stone with different cut may be imaged using the system 100 and method 200. In such embodiment, pavilion refers to the lower side and table refers to the upper side.

As shown at 504, a function of the movement of the cut stone 99 allows calculating a center of rotation movement and a tilt angle of the cut stone 99. Now, as shown at, the part that depicts the cut stone in the modeling image is segmented or sliced. For example, the image is cropped around the estimated center of rotation movement. Then, the image is filtered, for example using a high-pass filter and/or according to a certain threshold. This allows identifying the boundaries of the cut stone slice depicting in the modeling image.

As shown at 506, the cut stone slice is aligned according to the estimated angle of the cut stone 99.

As shown at 507, the cut stone slices from all the modeling images may now be arranged, for example according to an average diameter between two slices images from opposing angles. As used herein, opposite segments are images depicting the cut stone 99 from two opposing points of view so that the opposite segments are mirrored (except the distance from the image sensor 102). The images are arranged around the Z axis of the coordinate system, according to the rotation of the cut stone 99 in relation to the image sensor 102 along the motion scanning path.

This allows, as shown at 508, creating a volumetric model of the volumetric portion of cut stone 99 which is imaged in the current placement from all the cut stone slices. Optionally, the volumetric model is filled using a convex hull algorithm.

Optionally, the size of a cut stone segment 99 may be corrected by using an opposite cut stone segment 99, 180 degrees therefrom, and scaling the average diameters of both cut stone segment.

Optionally, an edge filter and/or identification of the lines density through "image close" morphological methods are used to refine the cropping.

Optionally, the an image of the cut stone 99 which is taken when the optical axis is on or parallel to the central axis of the cut stone 99 is used for creating the volumetric model and/or for leveling the segments.

Reference is now made, one again, to FIG. 5. Now, as shown at 204, a set of cut stone images are captured from a plurality of points of view along the surface of a virtual sphere surrounding the cut stone 99. Optionally, the horizontal and/or vertical angle difference between viewing angles of different images is between about 1° and about 4°, for example 1° horizontal angle difference and 3.6° vertical angle difference. Optionally, the cut stone images are taken between about −40° and about 90° in relation to a plane passing via the girdle. Optionally, the image sensor is maneuvered in a scanning pattern which is calculated such that is has a sine behavior of the center rotation movement along the X axis and superposition of sine (verAng)*Xamp and cosine(verAng)*Yamp in the Y movement when X amp is the X movement amplitude in a side set (verAng=0), and Yamp is the Y axis movement.

The images are captured by rotating the holder 101 and the image sensor actuator 103 so as to change the viewing angle of the image sensor 102 with respect to the surface of the cut stone 99. In each image, the optical axis of the image sensor 102 is directed to another point on the surface of the cut stone 99. This allows creating a volumetric image based on the volumetric model of the cut stone 99 in the current placement. The cropping process separates the segment of the image that depicts the cut stone 99 from the holder 101 and the background.

As described above, the cut stone 99 is placed on the holder, for example manually. Moreover, the scanning pattern of the image sensor 102 may vary according to the orientation of the cut stone 99, for example as described above. As such, the distance between the cut stone 99 and the image sensor 102 may but by fixed and/or known in advance. This deviation may be corrected during the rotation of the holder 101 and/or the image sensor, according to the estimated center of the rotation axis. Optionally, the correction is made by normalization of the size of the segment according a ratio of the diameter of the segment by an opposed slice diameter located 180° around the rotation circle. This opposed slice diameter outlines the stone from the other side, but at the same time has a similar contour.

Now, as shown at 205, the cut stone images of the cut stone in the current placement are cropped according to the respective volumetric model created in 203.

Figure 11:
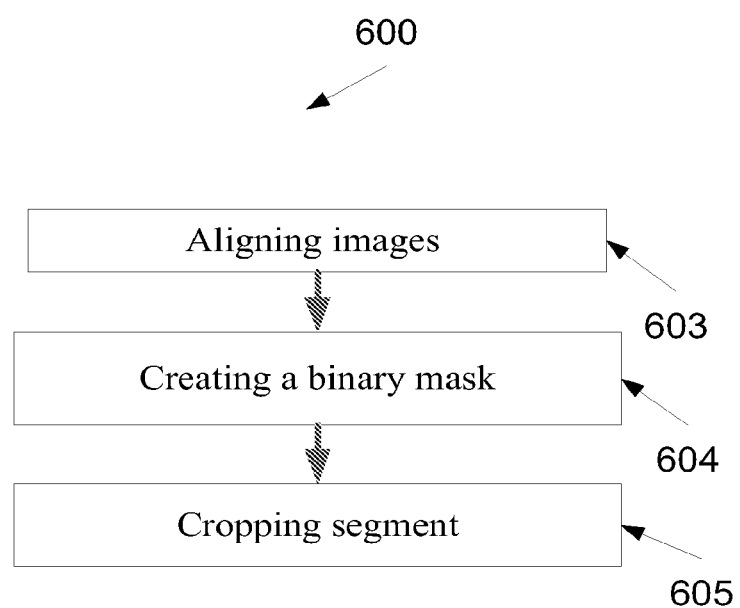
FIG. 11 is a flowchart of a cropping process in which a segment depicting the cut stone is identified and cropped, according to some embodiments of the present invention.

Reference is now made to FIG. 11, which is a flowchart 600 of a cropping process in which a segment depicting the cut stone 99 in its current placement is identified and cropped in a cut stone image, according to some embodiments of the present invention. This process is held in each one of the cut stone images.

First, as shown at 603, the image is aligned according to an estimated angle. The alignment is optionally performed according to the scanning pattern that is used for capturing the plurality of images.

Figure 12:
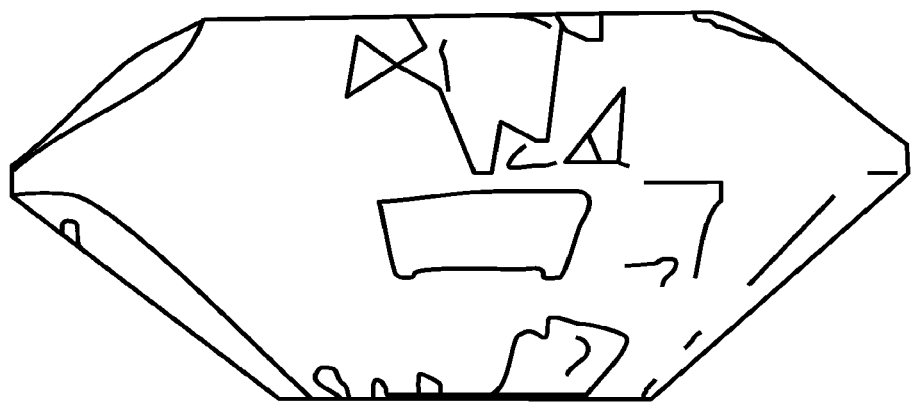
FIG. 12 is a flattened image of a cut stone segment taken from a rotated model thereof, according to some embodiments of the present invention.
Figure 13:
FIG. 13 is a binary mask of a cut stone segment, according to some embodiments of the present invention.

Now, as shown at 604, a binary mask for the segment is created from the volumetric model. The volumetric model is rotated to match the horizontal and vertical angle of viewing point depicted in the current cut stone image. Optionally, the origin location of the volumetric model is set such that the vertical angle=0°. In order to use the model for mask creation, it is rotated horizontally and vertically so that it fits the current image. The 3D rotated model is flattened to fit the 2D image, for example as shown in FIG. 12. The flattened model is than convhulled and filled. The result is a binary mask of the cut stone 99 that allows removing segments depicting the background and the holder 101, as shown at FIG. 13.

As shown at 605, the mask is used for crop the segment. Optionally, a new image is created by multiplying the segment by the binary mask. Optionally, artificial background is created by multiplying the background of the segment by (1-mask). The output of this process is an image depicting the cut stone 99 in the current placement without the background or the holder 101. Now, after all the cut stone images have been cropped, a plurality of cut stone segments of the cut stone in the current placement 99 from different angles is received. Optionally, these cut stone segments are combined to create a partial volumetric image of the cut stone 99 in its current placement. For example, the partial volumetric image may depict the cut stone 99 in a table up placement, as shown at FIG. 6A or the cut stone 99 in a pavilion up placement, as shown at FIG. 6B.

Optionally, the characteristics of the cut stone 99 are used for separating the cut stone 99 from the background, for example for creating the mask. Optionally, characteristics of the stones are manually provided, from example using a man machine interface (MMI), such as a keyboard which it connected to the system 100 and/or automatically provided for example using an image processing if the captured images and/or a scale which is connected to the holder. The characteristics may be the estimated light reflected from the stone, the light reflection strength, the color of the size, and/or its size. This allows refining the filters used to create the mask and/or edge detection process.

Now as shown at 206, the cut stone 99 is overturned so that the current placement thereof changes, for example from a table up placement to a pavilion up placement or vice versa. Blocks 202-205 are repeated when the cut stone 99 is in the current placement, which is now another placement. This allows creating two sets of cut stone segments, each arranged as a partial volumetric image of the cut stone 99. The first set depicts the cut stone 99, in a first placement, from a plurality of viewing angles and the second set depicts the cut stone 99, in a second placement, from a plurality of viewing angles. The first and second placements are optionally the pavilion up and the table up placements.

Now, as shown at 207, the cut stone segments of the cut stone in the first and second placements are now correlated. In such a manner, the horizontal and vertical angles of a certain cut stone segment in the partial volumetric image depicting the cut stone in the table up position, referred to herein as a table volumetric image, is correlated with a respective cut stone image having similar horizontal and vertical angles and taken from of the partial volumetric image depicting the cut stone in the pavilion position, referred to herein as a pavilion volumetric image.

Optionally, the correlation is performed in a multistep process. Optionally, the volumetric model created for the pavilion volumetric image and the volumetric model created for the table volumetric image are used. For brevity, these models are referred to herein as pavilion volumetric model and table volumetric model.

In every step of the correlation, the pavilion volumetric model is rotated by a fixed horizontal angle and unified with the table volumetric model. This rotation allows creating a unified volume of the two models. Correlation is achieved when the unified volume is minimal and the two models are coincided. First, the common parts from the table and pavilion volumetric models are identified and optionally extracted. Now, the pavilion volumetric model is turned to fit the shape of the table volumetric model. Then the pavilion volumetric model is rotated to in a delta horizontal angle. Unify table volumetric model with the rotated pavilion volumetric model. Optionally, each one of the table and the pavilion volumetric models is represented as a 3D point matrix. These matrixes are appended onto on another, for example by appending the 3D point matrix of the table volumetric model to the 3D point matrix of the rotated pavilion volumetric model. Optionally, the volume of the unified model is calculated for each optional correlation and the selected correlation is the correlation that has the minimal unified volume.

Additionally or alternately, the area surface of optional correlation between segments of the pavilion volumetric image and segments of the table volumetric image sliced images is used for detecting correlation. The data source for this correlation includes the cut stone segments sets of both the pavilion and table volumetric images, for example created as described above.

Now, a first segment of the set of segments of the pavilion volumetric image is shifted to be correlated with the last segment of the set of segments of the table volumetric image and a sequential segment becomes first segment. During this shifting the segments of the table volumetric image are not shifted. Now, each segment of the pavilion volumetric image is unified with a respective segment of the corresponding table volumetric image and a unified surface is calculated. The sum of all the unified surfaces is calculated and the result of this process represents a unified volume of the two volumetric images. This process is iteratively repeated n times for a set having n cut stone segments. The correlation is achieved when the unified volume is minimal, an indication that the two volumetric images coincide.

Additionally or alternately, the distance between the left and right edges, the width of the girdle and an angle between a line that connects the left and right edges 401 and the pavilion or the crown diameter is used for detecting correlation. The data for this correlation is distance, width, and/or angle vectors which are calculated above.

First, the best and second best correlation points between a distance vector of a segment of the pavilion volumetric image and a distance vector of a segment of the table volumetric image are found. The width and angle vectors may be used to determine which of the two is indicative of a real correlation and the exact location thereof. This defines the correlation and allows rotating the cut stone segments according to the correlation points. Optionally, the correlation is corrected by a visual indication by an operator. Optionally, the operator points at the approximate area and the precise point is determined by the best correlation in this area. Optionally, the bottom and/or up images are found using image registration techniques for finding a suitable picture for the bottom part.

Now, as shown at 208, partial volumetric images are merged to form a complete volumetric image of the cut stone 99. The volumetric image of the cut stone 99 includes a plurality of merged correlated segments, for example as depicted in FIG. 14. During this process partial and complementary images are combined into a single complete image of the cut stone 99 that includes parts which are not imaged by only one of the partial volumetric images. As described above, some parts of the cut stone 99 are covered during the scan. For example, the tip of the cut stone 99 may be placed in the holder 101, as shown in FIG. 3. By using segments from both the pavilion and table volumetric images, a full coverage of all the surface of the cut stone 99 is received. First, a merge mask which contains values in the range [0, 1] for defining the merge ratio of each pixel is created. The value of each pixel defines the proportions of the merge, where pixel with the value 1 indicates that the pixel is acquired from one set, for example the up set, 0 indicates that the pixel is acquired from another set, for example the down set.

This allows generating a volumetric image from one of the partial volumetric images and adding and/or replacing pixels from the other partial volumetric image according to a merge mask. Optionally, the merge mask is produced as follows:

First, a merge mask skeleton is created by initiate a merge mask with '0'. The dimensions of the merge mask skeleton are set according to the cropped images. Then, a girdle surface is extracted from griddle lines defined in one of the volumetric models. The girdle surface is marked in the mask. Now, the space between the girdle surface and the upper boundaries of the mask is filled with '1'. Pixels of the area are taken from the up set image solely. The bottom of the merge area is located in the pavilion model. This stage point represents the stage and should not appear in the result. The girdle line is duplicated from the girdle line to the area of the cut stone 99 stage point, while its value is attenuated from 1 to 0 in order to have a gradient image.

Below the stage point, the mask remain zeroed, this area will be taken from the pavilion image solely, for example see FIG. 15.

The segments of the pavilion volumetric image are multiplied by the merge mask, pixel by pixel and the segments of the table volumetric image are multiplied by 1−(merge mask). The result of the two multiplications is summed pixel by pixel giving the merged image. FIG. 16 depicts an image taken from the merged volumetric images.

Now, as shown at 209, the volumetric image may be presented to the viewer, allowing her to view the cut stone 99 from any of the plurality of viewing angles from which the images depicting the cut stone segments where taken. This allows using a pointing device, such as a mouse or a touch screen, to rotate the cut stone 99, changing the display from displaying one viewing angle to another viewing angle. The cut stone 99 may be presented on any client terminal, such as a personal computer, a tablet, a cellular phone, a Smartphone, a laptop and the like.

The rotation instructions are translated to a change in the merged segment of the volumetric image which is currently displayed to the user. The volumetric image may be provided as an independent file, a set of a plurality of files, each represents a different merged segment and the like.

According to some embodiments of the present invention, the system 100 is used to examine automatically other aspects of the cut stone 99. For example an image processing module may be added to evaluate color, fluorescence, and/or cut according to known methods. Optionally, proportion valuation is done by using frequency spreading of the stone's shape, fitting the stone to it in different angles in order to evaluate the symmetry. Optionally, scales are used to evaluate weight.

According to some embodiments of the present invention, the system 100 is used to authenticate the cut stone 99. For example, thermal conductivity examination may be done and/or a specific gravity examination by visual volume identification and/or weighing. The thermal conductivity examination may be done using adapted sensors known in the art.

According to some embodiments of the present invention, the system 100 is also used to identify the cut stone 99. As described above, the volumetric image depicts the gemstone 99 from a plurality of viewing angles and therefore includes unique visual data about it, for example the clarity and/or exact cuts and/or impurities thereof. This unique data may be analyzed to identify the cut stone 99. For example, the volumetric image of a derivative thereof may be matched with a database of identified volumetric images and/or derivatives thereof. The identification process may combine other characteristic identification, such as weight.

It is expected that during the life of a patent maturing from this application many relevant systems and methods will be developed and the scope of the term image processing, module, image sensor, light source, and computing unit is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of imaging a cut stone having a girdle, comprising:
    a) obtaining, in a first placement of the cut stone, a first volumetric model of a first part of the cut stone, including the girdle, and taking a plurality of first images of the first part of the cut stone from a plurality of viewing directions, each defined by its horizontal and vertical angles relative to a plane passing via the girdle;
    (b) obtaining, in a second placement of the cut stone, a second volumetric model of a second part of the cut stone, including the girdle, and taking a plurality of second images of the second part of cut stone from a plurality of viewing direction, each defined by its horizontal and vertical angles relative to said plane passing via the girdle;
    (c) correlating the second images with the first images using the first and second volumetric models, based on the horizontal and vertical angles, to obtain correlated images of the first and second parts of the cut stone, with a unified volume of the first volumetric model and the second volumetric model being minimal and the first volumetric model and the second volumetric model coinciding;
    (d) generating a volumetric image of the cut stone by merging segments cropped from the correlated images of the first and second parts of the cut stone; and
    (e) outputting said volumetric image so as to allow a viewer to view the cut stone with its first and second parts as imaged from the plurality of viewing directions.

2. The method according to claim 1, wherein said first part of the cut stone includes the cut stone's table and girdle, and the second part includes the cut stone's pavilion and girdle.

3. The method according to claim 1,
    wherein the step (a) includes obtaining a plurality of first modeling images of the first part of the cut stone and using the modeling images for generating the first volumetric model of the first part of the cut stone;
    wherein the step (b) includes obtaining a plurality of second modeling images of the second part of the cut stone and using the modeling images for generating the second volumetric model of the second part of the cut stone; and
    wherein the using in steps (a) and (b) of the first and second volumetric models is for calculating scanning patterns; and
    wherein the using of the scanning patterns is for maneuvering according to them at least one of a holder of the cut stone and at least one image sensor for capturing, by the at least one image sensor, the first and the second images of the first and second parts of the cut stone, respectively.

4. The method according to claim 3, wherein the maneuvering is performed by rotating the cut stone around a first rotation axis, and rotating the at least one image sensor around a second rotation axis, being perpendicular to the first rotation axis.

5. The method according to claim 3, wherein the maneuvering is performed so as to allow imaging the cut stone from any point on a surface of a virtual sphere around the cut stone.

6. The method according to claim 3, wherein the maneuvering is performed under such illumination of the cut stone that allows to avoid an effect of direct reflection of light from surfaces of the cut stone.

7. The method according to claim 3, wherein the same image sensor that is used for capturing modeling images for the creation of the volumetric models is maneuvered for capturing the first and the second images.

8. A system of imaging a cut stone having a girdle, the system comprising:
    a holder for mounting the cut stone in first and second placements;
    at least one image sensor;
    an image sensor actuator configured to maneuver the at least one image sensor for capturing a plurality of first images of a first part of the cut stone in its first placement and a plurality of second images of a second part of the cut stone in its second placement; each of the first and second parts of the cut stone, including its girdle, and the first and second images of these parts being taken from a plurality of viewing directions, each defined by a horizontal and a vertical angles relative to a plane passing via the girdle;
    an image capturing module configured to correlate the second images with the first images using a first volumetric model of the first part of the cut stone and a second volumetric model of the second part of the cut stone, based on the horizontal and vertical angles, to obtain correlated images of the first and second parts of the cut stone, with a unified volume of the first volumetric model and the second volumetric model being minimal and the first volumetric model and the second volumetric model coinciding, and to crop segments from the first and second images;
    a reconstruction module for generating a volumetric image of the cut stone by merging segments of the correlated images of the first and second parts of the cut stone; and
    an output unit which outputs said volumetric image to allow viewing the cut stone from a plurality of viewing angles.

9. The system according to claim 8, wherein the image capturing module is configured for using the first and second volumetric models of the cut stone created in its respective first and second placements, for the correlation between the first and second images having similar horizontal and vertical angles relative to the plane passing via the girdle.

10. The system according claim 9, wherein the image capturing module is configured to compute the first volumetric model of the first part of the cut stone and the second volumetric module of the second part of the cut stone, and to use the volumetric models for computing first and second scanning patterns, and the system further comprises a controller, which instructs the holder and the image sensor actuator to respectively maneuver the image sensor and rotate the cut stone in each of the first and second placements according to the respective first and second scanning patterns.

11. The system according to claim 8, wherein the holder is configured for rotating the cut stone around a first rotation axis, the image sensor actuator being configured for rotating the image sensor around a second rotation axis, the rotating of both the holder and the image sensor being configured to provide the viewing directions during the maneuvering, which the viewing directions include, in one of the first and second placements, a direction facing the cut stone's table facet, and in the other of the first and second placements, a direction facing the cut stone's pavilion.

* * * * *